(12) United States Patent
Saranzak et al.

(10) Patent No.: US 12,644,062 B2
(45) Date of Patent: *Jun. 2, 2026

(54) BELLY BLADE MOUNTED TO CENTER OF MOWER EQUIPMENT

(71) Applicants: Robert Saranzak, Lake Zurich, IL (US); Donald Saranzak, Spring Grove, IL (US)

(72) Inventors: Robert Saranzak, Lake Zurich, IL (US); Donald Saranzak, Spring Grove, IL (US)

(73) Assignee: Arlington Power Equipment, Inc., Palatine, IL (US)

( * ) Notice: Subject to any disclaimer, the term of this patent is extended or adjusted under 35 U.S.C. 154(b) by 427 days.

This patent is subject to a terminal disclaimer.

(21) Appl. No.: 18/197,468

(22) Filed: May 15, 2023

(65) Prior Publication Data

US 2023/0279303 A1     Sep. 7, 2023

Related U.S. Application Data

(63) Continuation of application No. 16/753,547, filed on Apr. 3, 2020, now abandoned.

(51) Int. Cl.
| | |
|---|---|
| *E01H 5/06* | (2006.01) |
| *B01J 21/04* | (2006.01) |
| *B01J 21/06* | (2006.01) |
| *B01J 21/18* | (2006.01) |
| *B01J 23/30* | (2006.01) |
| *C07C 67/03* | (2006.01) |
| *C10L 1/02* | (2006.01) |
| *C11C 1/06* | (2006.01) |
| *C11C 3/10* | (2006.01) |

(52) U.S. Cl.
CPC ................. *C10L 1/02* (2013.01); *B01J 21/04* (2013.01); *B01J 21/066* (2013.01); *B01J 21/18* (2013.01); *B01J 23/30* (2013.01); *C07C 67/03* (2013.01); *C11C 1/06* (2013.01); *C11C 3/10* (2013.01); *E01H 5/061* (2013.01); *C10L 2200/0484* (2013.01)

(58) Field of Classification Search
CPC ................................ E01H 5/061; E01H 5/063
See application file for complete search history.

(56) References Cited

U.S. PATENT DOCUMENTS

| | | | | |
|---|---|---|---|---|
| 8,360,165 | B2 * | 1/2013 | Leith ...................... | E02F 3/764 172/821 |
| 9,603,303 | B2 * | 3/2017 | Hoppel .................. | A01D 34/64 |
| 11,649,598 | B2 * | 5/2023 | Saranzak ................. | E01H 5/06 37/241 |

(Continued)

*Primary Examiner* — Matthew R Buck
(74) *Attorney, Agent, or Firm* — Vitale, Vickrey, Niro, Solon & Gasey LLP

(57) ABSTRACT

The present disclosure relates to improvements in snow removal vehicles. A vehicle is disclosed, wherein the vehicle may have a reduced turning radius, or a zero-turn radius. The present disclosure also relates to improvements in snow shovels attached to the vehicle, including disclosure directed to a snow shovel mounted to the middle of the vehicle, rather than to the vehicle's front. Further yet, the present application discloses a snow shovel which is interchangeable with a mower attachment, thereby allowing a vehicle to be used as a snow plow or as a mower.

27 Claims, 7 Drawing Sheets

(56)                  References Cited

U.S. PATENT DOCUMENTS

2010/0164202 A1*   7/2010   Dilworth ............. A01B 59/064
                                              280/477
2014/0173946 A1*   6/2014   Gerrits ..................... E02F 9/16
                                              56/14.7
2017/0254035 A1*   9/2017   Rich ....................... E01H 5/062

* cited by examiner

BELLY BLADE MOUNTED TO CENTER OF MOWER EQUIPMENT

PRIORITY INFORMATION

This application is a Continuation of Ser. No. 16/753,547, filed Sep. 17, 2019, now U.S. Pat. No. 11,649,598 issued May 16, 2023.

FIELD OF THE INVENTION

The present inventions relate to the field of snow removal, and more specifically, to devices and methods for improving snow removal utilizing standard lawn equipment and riding lawn mowers. Among other things, the disclosed inventions provide snow removal vehicles having improved control, handling, turning radius, which more effectively remove snow, and have additional benefits as will become apparent herein.

DESCRIPTION OF RELATED ART

It is often necessary to remove snow from hard, paved surfaces, in order to allow ingress and egress on public or private property. Brooms, shovels, snow blowers, and plows are popular tools for such removal. In some instances, zero-turn lawn mowers and riding lawn mowers are fitted with plow shovels, where the plow shovel is mounted to the front of the lawn mower and manually operated. Disadvantageously, such a configuration allows for relatively less leverage on the plow shovel. As a result, there is a need for a configuration which provides increased leverage on the plow shovel to increase the ability to remove snow from a surface, while also maintaining a tight turning radius.

BRIEF SUMMARY OF THE INVENTIONS

Embodiments of the inventions improve upon prior art methods and devices by providing a vehicle having an improved ability to remove snow from a surface, while also maintaining a tight turning radius.

Embodiments of the inventions are directed to a vehicle for removing snow, the vehicle comprising a frame; a pair of front wheels, the pair of front wheels comprising a left front wheel mounted on the left side of a forward portion of the frame; and a right front wheel mounted on the right side of the forward portion of the frame; a pair of rear wheels mounted to a rear portion of the frame; an engine mounted to the frame coupled to one of the pair of front wheels or rear wheels; a plow shovel, the plow shovel being mounted to the frame between the pair of front wheels and the pair of rear wheels; and an adjustment mechanism mounted to the frame and affixed to the plow shovel wherein the adjustment mechanism is configured to maneuver the position of the plow shovel in relation to the frame.

In some embodiments, the adjustment mechanism further includes a first hydraulic for controlling the position of the plow shovel. The adjustment mechanism may further include a second hydraulic for controlling the position of the plow shovel. The first and second hydraulics may be controlled by a user-operated lever.

Some embodiments provide a vehicle control, wherein the vehicle control may be at least one steering rod. The vehicle may optionally be a zero-turn radius vehicle, such as a riding lawn mower. The vehicle may be power by a gas engine, wherein the gas engine is connected to an air intake and an exhaust, and wherein the air intake and the exhaust are mounted behind a seat mounted to the frame.

In some embodiments of the invention, the plow shovel is removably mounted to the frame, and further, the plow shovel may be interchangeable with a mower attachment.

Further yet, additional embodiments of the inventions are directed to a vehicle for removing snow, the vehicle comprising a vehicle frame of a lawn mower having a removable mower deck; a pair of front wheels mounted to the vehicle frame and a pair of rear wheels mounted to the vehicle frame; an engine mounted to the vehicle frame and coupled to one of the pair of front wheels or the pair of rear wheels to capable of powering the vehicle; a belly blade apparatus moveably fastened to the vehicle frame in the general location of the mower deck between the pair of front wheels and the pair of rear wheels; a belly blade apparatus including a body having a snow blow mount and a frame mount wherein the belly blade apparatus is mounted to the vehicle frame at the frame mount; the belly blade apparatus including a snowplow blade rotatably affixed to the snowplow mount of the belly blade body by a hinge mechanism; a hydraulic cylinder affixed to the belly blade body and the snowplow blade, wherein the hydraulic cylinder is configured to rotate the blade about the rotatable hinge about a first axis relative to the frame; a trip spring affixed to the snowplow blade and the belly blade frame; and a mechanism to move the snowplow blade about a second axis relative to the frame.

In some embodiments, the front wheels and the rear wheels are configured in a manner that the vehicle operates in a zero-radius turn. The vehicle frame of the lawn mower may be configured as a riding mower, and the vehicle frame may be configured as a stand-on power mower. The pair of rear wheels can be larger relative to the pair of front wheels, and an alternator may be provided, with lights powered by the alternator.

Optionally, the vehicle for removing snow may include a frontend weight box affixed to the vehicle frame. The front wheels and rear wheels may be soft-tread aggressive drive tires for additional traction. Further yet, vehicle controls may be provided, including at least one steering rod. The snowplow blade may be positioned mid-way between the front wheels and the rear wheels at the center of gravity of the vehicle.

Therefore, it is an object of the inventions to provide a vehicle with improved ability to remove snow, including, without limitation, an improvement in the vehicle's turning radius.

It is a further objective of the inventions to provide a tight turning radius, allowing operators to have more precise control over their snow shoveling. In some embodiments, it is an objective to provide a vehicle with a zero-turn radius.

A further objective of the inventions is to allow vehicles, such as riding mowers, to be used year-round by interchanging a mower attachment with a plow shovel.

DRAWINGS

DETAILED DESCRIPTION OF THE PREFERRED EMBODIMENTS

Figure 1:
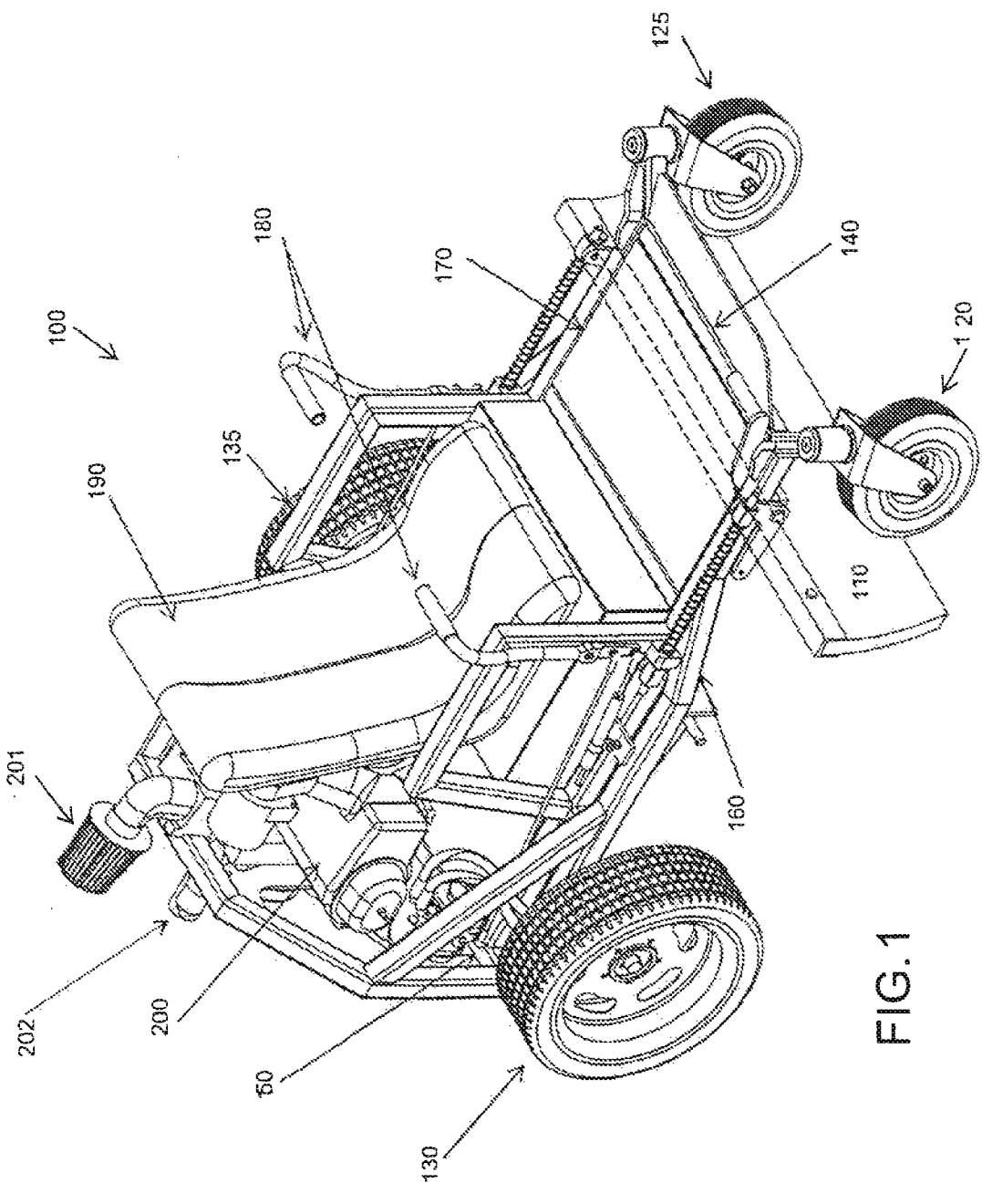
FIG. 1 is a perspective view an embodiment of a zero-turn snow removal vehicle.

Before any embodiments of the invention are explained in detail, it is to be understood that the inventions are not limited in their application to the details of construction and/or arrangement of components set forth in the following description or illustrated in the following drawings. The invention is capable of other embodiments, and of being practiced or carried out in various ways. Also, it should be understood that the phraseology and terminology used herein should not be regarded as limiting the scope of the inventions unless explicitly stated.

The following discussion is presented to enable a person skilled in the art to make and use embodiments of the inventions. Various modifications to the illustrated embodiments will be readily apparent to those skilled in the art. Thus, embodiments of the invention are not intended to be limited to the embodiments shown but are to be accorded the widest scope consistent with the principles and features disclosed herein. The following detailed description is to be read with reference to the figures, in which the elements in different figures have life reference numerals. The figures, which are not necessarily to scale, depict selected embodiments and are not intended to limit the scope of embodiments of the inventions. A person having ordinary skill in the art will recognize the examples provided herein have many useful alternatives and fall within the scope of embodiments of the invention.

The present disclosure is generally directed to an apparatus and method for improving snow removal. The inventions provide a zero-turn vehicle 100 having a plow shovel mechanism 110 mounted in the belly location between a pair of front wheels 120, 125, and a pair of back wheels 130, 135. The plow shovel mechanism 110 is typically mounted in the same location as the mower deck in a zero-turn vehicle 100. In embodiments of the invention, the mower deck may be removed and the plow shovel mechanism 110 may be mounted in place of the mower deck. Both the pair of front wheels and the pair of back wheels may include a left and a right wheel, respectively. The inventions improve the amount of snow that a plow shovel can push aside, and the efficiency with which snow is pushed aside. Moreover, the inventions provide improved handling and control over a zero-turn vehicle.

Generally speaking, the inventions may relate to the use of a zero-turn vehicle 100 for snow removal. Zero-turn vehicles are known in the context of, for example, zero-turn lawn mowers. A zero-turn vehicle is typically characterized by its front wheels extending to the front edge of the vehicle, thus allowing the vehicle to make a "zero radius" turn. In other words, placement of the front wheels at the front edge of the vehicle creates a relatively highly narrow turning radius, which is sometimes described as "turning in place."

While the preferred embodiment focuses on zero-turn vehicles, the plow shovel mechanism 110 or belly bade 304 may be mounted on other types of equipment. The key feature is that the plow shovel mechanism 110 or belly blade apparatus 304 is mounted in a generally centralized location between a front pair of wheels 120, 125 and a back pair of wheels 130, 135. As such, the plow shovel may be used in connection with a stand-on riding mower; a float deck-walk behind mower; a riding mower or any piece of equipment in which a belly mount blade can be configured between the front set of wheels and a rear set of wheels. It should be understood that the use of the plow shovel mechanism 110 or belly blade apparatus 304 is not limited to only the zero-turn mower configuration, the description of the zero-turn mower configuration is for exemplary purposes only. A person of ordinary skill in the art would appreciate how the plow shovel mechanism 110 or belly blade apparatus 304 may be mounted on stand-on mowers, float deck mowers, riding mowers and the like of the cradle where the mower equipment is typically mounted.

In FIG. 1, front wheels 120, 125 are shown mounted (using a rotatable hinge, or any other fastener for allowing the front wheels 120, 125 to turn) in the forward-most position on vehicle. FIG. 1 shows a vehicle having a frame, wherein the vehicle's frame has a forward edge and a rear edge (obscured). Front wheels are positioned along the forward edge 140 of the vehicle's frame. Additionally, front wheels 120, 125 are mounted on the corners of the forward edge of the frame; that is to say, left front wheel 125 is mounted to the left corner of the forward edge of the frame, and right front wheel 120 is mounted to the right corner of the forward edge of the frame. Rear wheels 130, 135 are positioned along the rear edge 150. The frame's forward edge 140 and rear edge 150 may be connected by side rails 160, 170. However, it should be understood that possible embodiments of the inventions have different frame configurations, including frames in which the front wheels 120, 125 which are not necessarily configured in the forward-most position 140 of the vehicle, and/or rear wheels 130, 135 which are not necessarily positioned on the rear edge 150 of the vehicle frame. Embodiments in which front wheels 120, 125 are offset from vehicle's forward-most position will have a longer turning radius but are nonetheless intended to be within the scope of the present inventions.

Prior art vehicles in which a plow shovel is mounted to the front of the vehicle suffer from the disadvantage that, when plowing snow, the force of the snow against the plow shovel can create an "upward" force, which results in less effective, and/or less efficient, snow plowing. Embodiments of the invention thus counteract such an upward force by configuring the plow shovel under the frame, between the front and rear wheels, resulting in improved leverage on the plow shovel and by extension, an improved snow plowing experience.

In FIG. 1, rear wheels 130, 135 are shown to be larger in radius then front wheels 120, 125. The relatively larger rear wheels 130, 135 may provide improved control over the vehicle 100, especially during snowy or icy conditions. The wheels 120, 125, 130, 135 may be fitted with soft tread aggressive drive tires to provide additional traction. In some embodiments, rear wheels 130, 135 may also be wider in width than front wheels 120, 125. Front wheels 120, 125 may be pivotable to enable steering. It is contemplated that embodiments of the inventions include vehicle controls sufficient to control the speed and direction of the vehicle 100. For example, vehicle 100 may have a steering wheel or steering rods 180, or any other known steering mechanism. In addition to steering, in some embodiments of the inventions, the vehicle controls further include a throttle or pedal for controlling speed of the vehicle, including, in some embodiments, a gas pedal and/or brake pedal. In some embodiments of the inventions, vehicle controls further include a control lever for changing the direction of plow shovel, discussed further below.

A seat 190 may be provided, allowing operators of the vehicle 100 to sit on the vehicle 100 while operating it. The seat 190 may be attached to the frame, and vehicle controls may be conveniently positioned to allow a user to operate them easily. An air intake 201, gas engine 200, and exhaust 202 may be provided for powering the vehicle. In embodiments, the air intake 201, gas engine 200, and exhaust 202 may be positioned behind the seat 190 or under the seat 190. The gas engine 200 may be coupled to the rear wheels 130, 135 and power the rear wheels 130, 135, and, in other embodiments, may power the front wheels 120, 125 instead of, or in addition to, the rear wheels 130, 135.

The vehicle 100 may also be fitted with certain accessories to enhance the snow removal operation. For example, the engine 200 may be fitted with an alternator and light kit. The light kit (not shown) could be mounted on the forwardmost position 140 of the vehicle 100. There may be one or two lights mounted at the forward-most position 140. Additionally, a light may be mounted at the rear edge 150 of the vehicle 100. The lights operate to help illuminate the area being plowed. The vehicle 100 may also be fitted with a safety beacon or strobe light (not shown) which illuminate during operation of the vehicle such that the vehicle is more visible to others. The vehicle could be fitted with a front end weight box along forward-most position 140 of the vehicle 100. The weight box operates to help evenly distribute the weight such that the center point of the weight distribution corresponds to the general location of the blow blade mechanism 111. The vehicle 100 could also be fitted with Mini Sno-Ex salt spreaders on the forward-most position 140 or the rear edge 150. Additionally, the vehicle could be fitted with hand covers and heaters at the controls 180 to provide warmth and comfort to the user.

In embodiments of the inventions, a plow shovel mechanism 111 may be affixed to the frame of vehicle, for example by mounting the plow shovel mechanism 111 to the left rail 170 and the right rail 16. Further yet, in embodiments of the inventions, the plow shovel mechanism 111 may be affixed to the frame at a position between the forward edge 140 of the frame and the rear edge 150 of the frame, such that the plow shovel mechanism 111 is affixed to the frame behind front wheels 120, 125. Positioning the plow shovel mechanism 111 behind the front wheels 120, 125 provides advantages over prior art vehicles in which the plow shovel is mounted in front of front wheels. For example, positioning the plow shovel mechanism 111 behind front wheels 120, 125 allows the vehicle 100 to maintain its "zero-turn radius." thereby allowing the vehicle 100 to maneuver through tighter environments with improved control. The position of the plow shovel mechanism 111 behind the front wheels 120, 125 allows the vehicle 100 to maintain a relatively tight turn radius as compared to embodiments in which the plow shovel is mounted in front of the front wheels. Thus, using embodiments of the invention, it is possible to configure a vehicle to plow show while maintaining a zero-turn radius. And, even if the radius is not a true "zero-turn," embodiments of the inventions can still provide a reduced, tighter turn radius.

Additionally, in embodiments of the inventions, the weight of vehicle 100 may be distributed through the frame and to the front wheels 120, 125. Weight may be closely distributed equally to the front and rear wheels, or the rear wheels 130, 135 may carry a greater portion of the vehicle's weight relative to the front wheels 120, 125. Regardless, the weight of the vehicle 100 through the frame creates additional "downward" pressure on the plow shovel 110 (which is mounted between the front and rear wheels), which thereby increases its leverage relative to embodiments in which the plow shovel mechanism 111 is mounted to the front of the vehicle 100. That is to say, by positioning the plow shovel mechanism 111 behind the front wheels 120, 125, embodiments of the invention provided increased leverage to the plow shovel mechanism 111 and allow the plow shovel 110 to shovel more snow relative to embodiments wherein the plow shovel is mounted to the front of the vehicle.

Figures 2, 3:
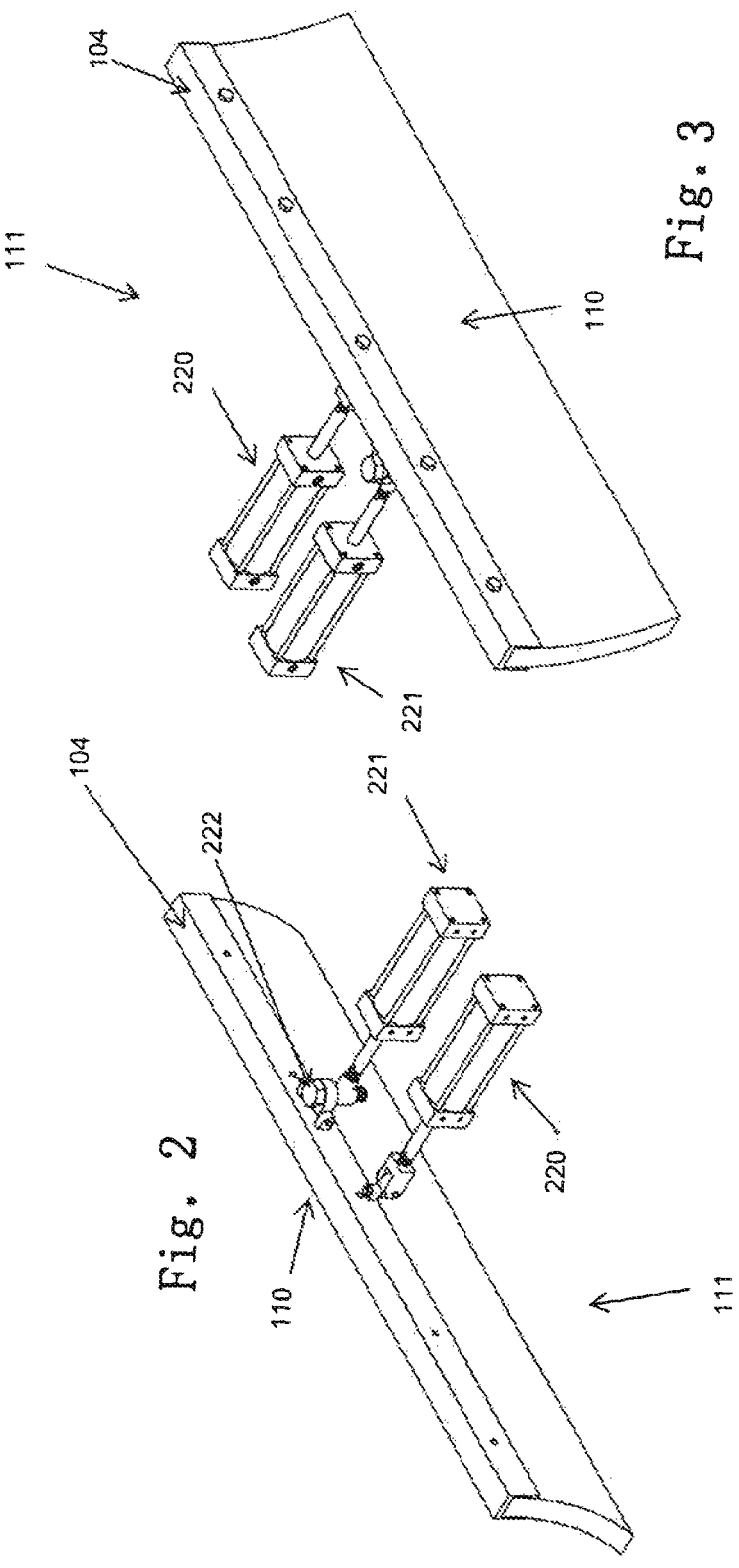
FIG. 2 is a back view of a plow shovel controlled by hydraulics.
FIG. 3 is a front view of a plow shovel controlled by hydraulics.
Figure 4:
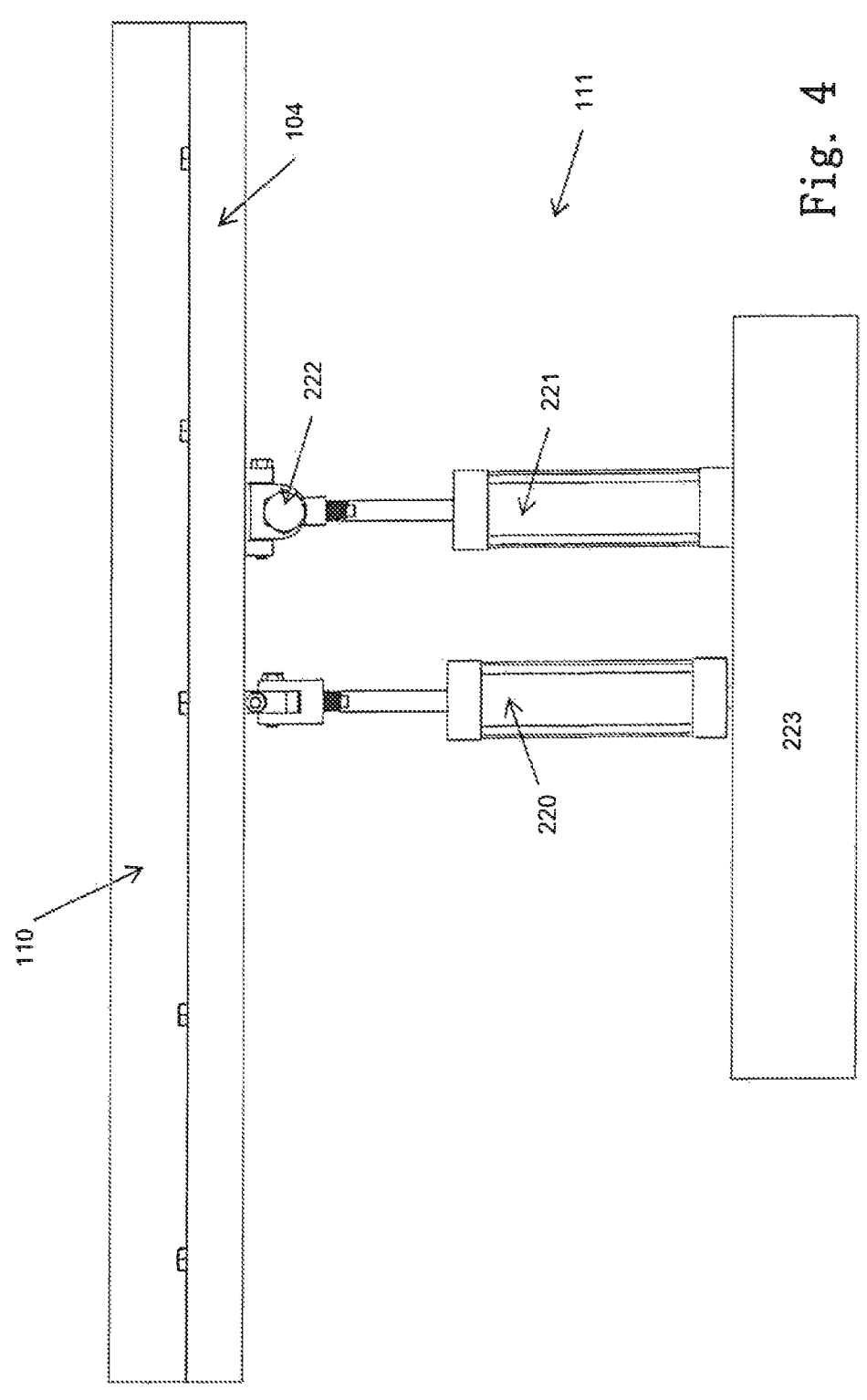
FIG. 4 is a top view of a plow shovel controlled by hydraulics.

FIGS. 2, 3 and 4 show an embodiment of the plow shovel mechanism 111. The plow shovel mechanism 111 includes a plow shovel 110 which is capable of moving the snow along the blade of the plow shovel 110. The plow shovel 110 may be constructed of steel, aluminum, plastic, vinyl or other suitable material. The plow shovel 110 includes a snow deflector 104 which may also be used to attach the plow blade 110 to a hydraulic piston 220. The hydraulic piston 220 operates to move inward or outward to adjust the position of the blade 110 with respect to the frame of the vehicle 100. The blade mechanism 111 further includes a stabilizing bar 221. The stabilizing bar 221 may be rotatably connected to the plow blade 110 and attached to a hinge 222 positioned on the snow deflector 104 attached to the blade 110. Alternatively, the stabilizing bar 221 could be a second hydraulic piston as shown in FIGS. 2 and 3. The plow blade mechanism 111 includes a mount frame 223 to which the first hydraulic piston 220 and the stabilizing bar 221/second hydraulic piston 221 are attached.

Figures 5, 6:
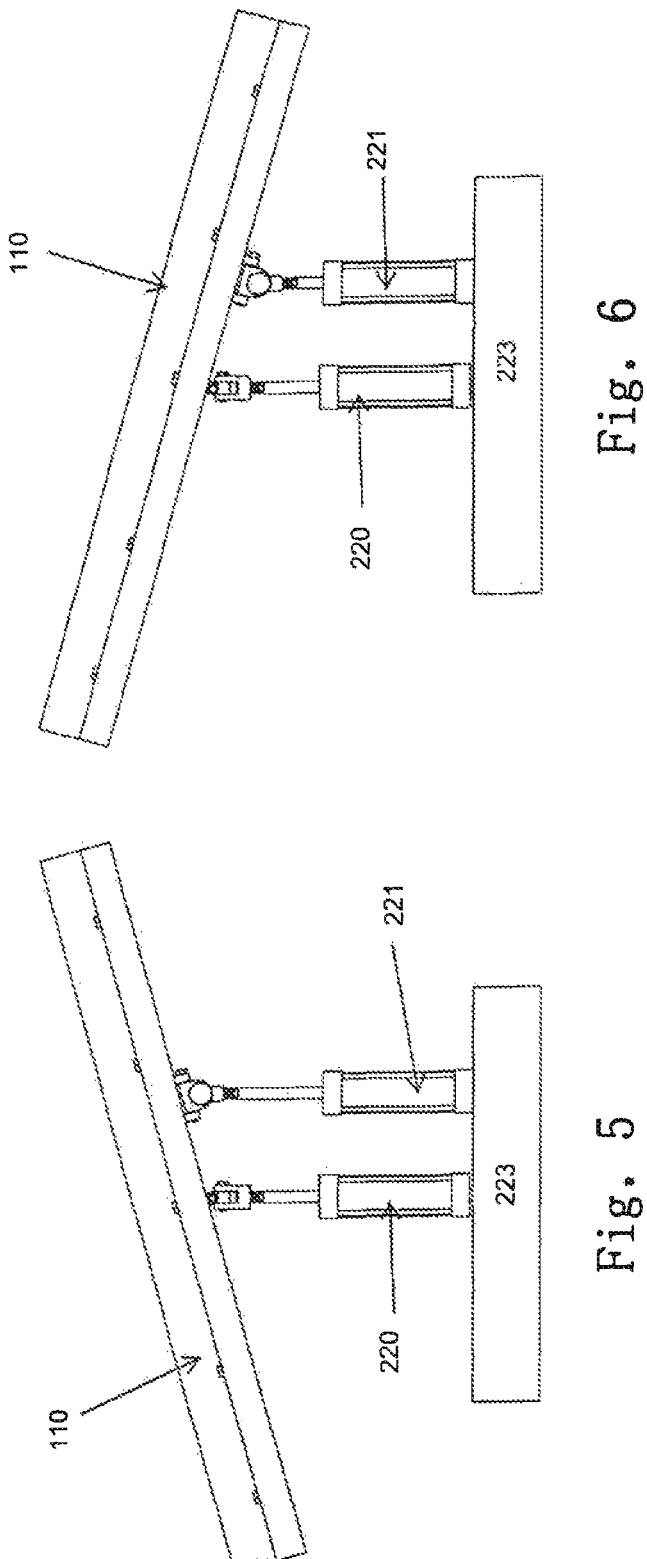
FIG. 5 is a top view of a plow shovel in a left position.
FIG. 6 is a top view of a plow shovel in a right position.
Figure 7:
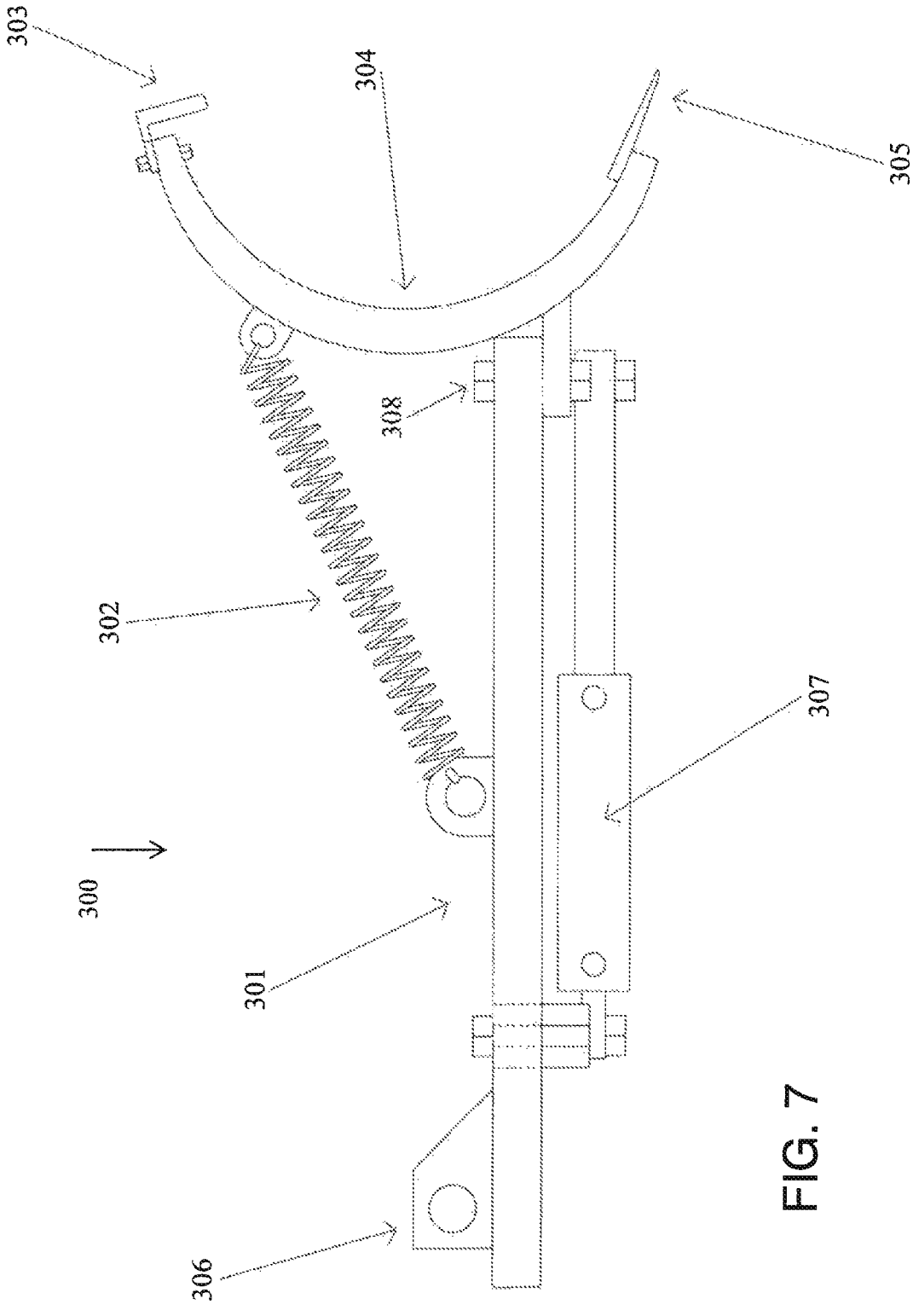
FIG. 7 is a side view of an alternative design for a belly mounted blade.

Further yet, in some embodiments, the plow shovel may be pivoted from a straight position (FIG. 4) to a left position (FIG. 5) or a right position (FIG. 6). Control over the plow shovel 110 may be manual. In such embodiments, a user may slide the plow shovel 110 into the desired position and then fasten it using known fasteners. In other embodiments, control over the angle of the plow shovel 110 is achieved using control levers that operate hydraulics 220, 221. Such control levers may be positioned near the seat 190, together with other vehicle controls.

FIGS. 7, 8, 9 and 10 depict an alternative blade arrangement that may be used as alternative to the plow shovel 110 described in the previous figures. This attachment may bolt in place of a mower deck on a variety of equipment. Hydraulically operated, this belly blade attachment can convert a summer riding mower to an efficient sidewalk snowplow machine. The attachment can partially be removed and mower deck put in place for summer use. Converting a ZTR mower into an all year-round revenue producer.

Figure 8:
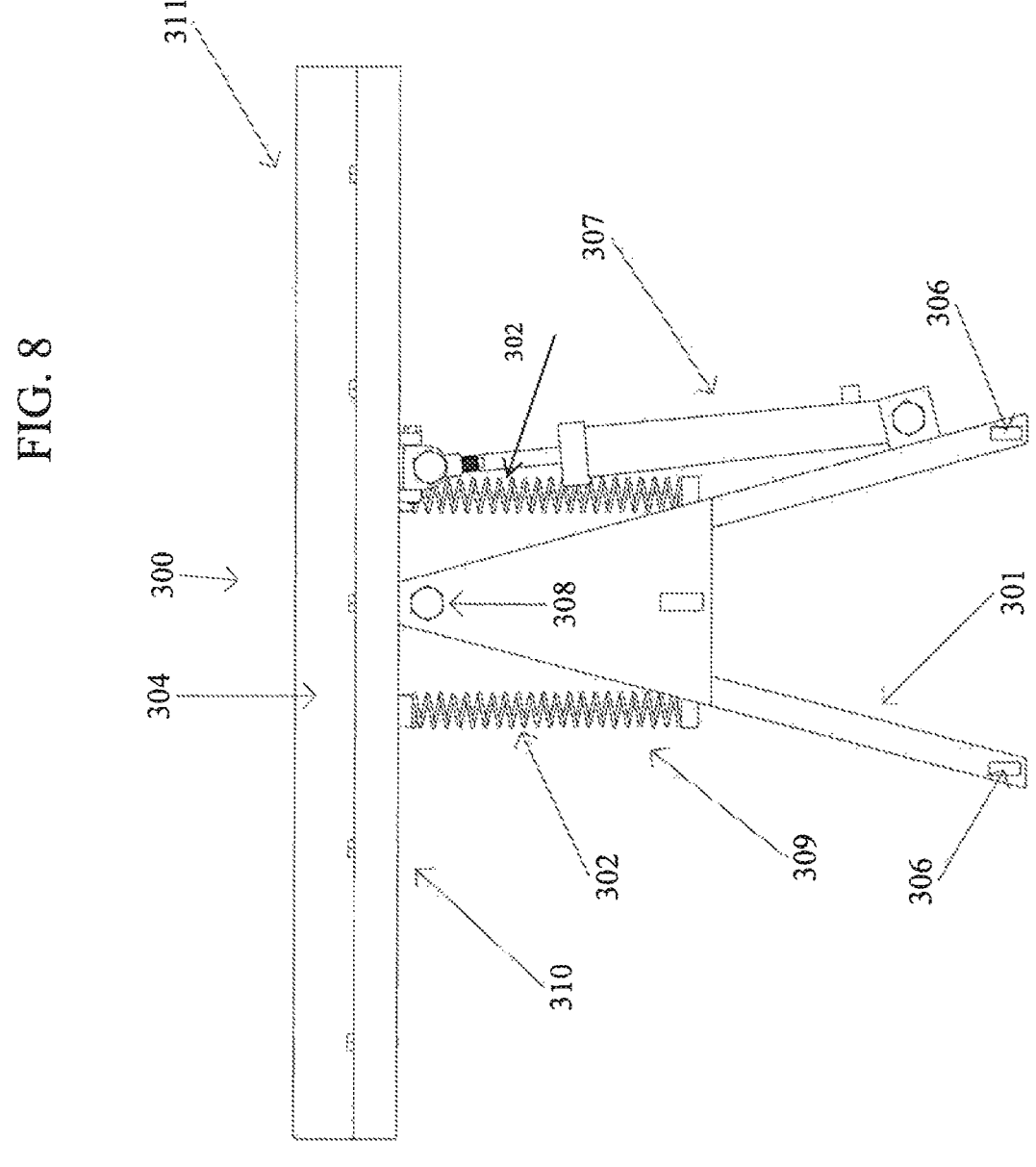
FIG. 8 is a top view of an alternative design for a belly mounted blade.
Figures 9, 10:
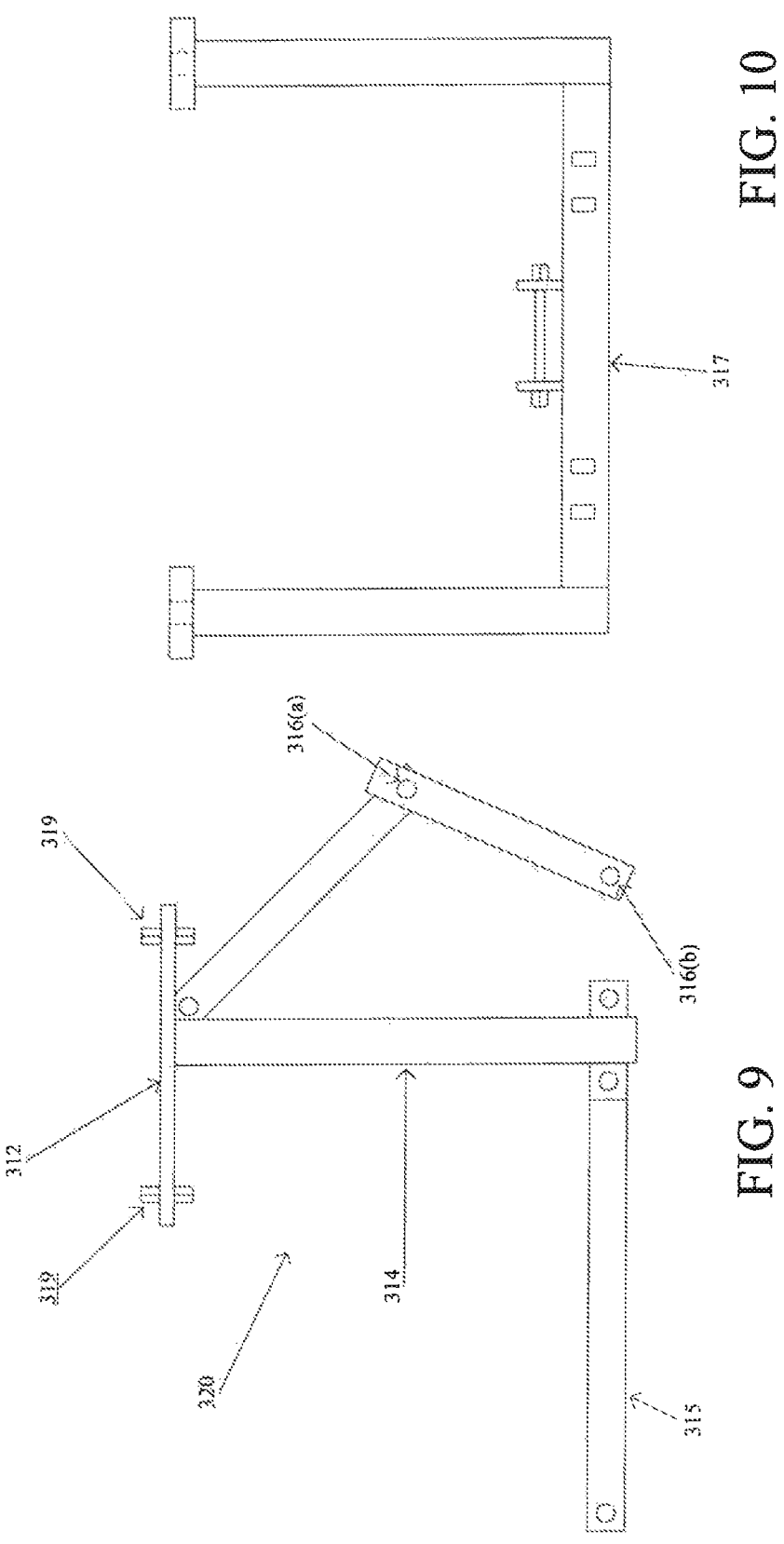
FIG. 9 is a side view of a mounting frame for a belly mounted blade.
FIG. 10 is a front view of a mounting frame for a belly mounted blade.

FIGS. 8 and 9 show a side view and a top view of a belly blade plow 300 configuration. The belly bade 304 may be configured in a generally C-shaped configuration to deflect the snow along the length of the belly blade 304. The shape of the blade could be of any configuration such as V-shaped, straight, L-shaped, modl-board configuration, or any other known blade shapes. The belly blade 304 has a steel cutting edge 305 mounted to the lower portion of the belly blade 304. The cutting edge 305 may be made of plastic, vinyl or other suitable material. The cutting edge 305 may be mounted to the belly blade using any known type of fastener including but not limited to glue, bolts, fasteners, etc. The belly blade 304 may also including a snow deflector 303 mounted to the belly blade. The snow deflector 303 may be made of rubber, aluminum, steel, plastic, vinyl or other suitable material and can be fastened to the belly blade 304 using a bolt, screw, fastener, glue or other fastening technique.

The belly blade plow 300 includes a plow frame 301. The frame is mounted to the under-belly of a lawn mower 100 in FIG. 1 by means of plow mounting tabs 306. The belly blade plow 300 is held in place to the mounting bracket of the zero-turn 100 by amounting bracket on the side rails 160, 170. A plow blade trip spring 302 is mounted to the belly blade 304 and the plow frame 301. A hydraulic turn cylinder 307 is also mounted to the belly blade 304 and the plow frame 301. While a hydraulic turn cylinder 307 is shown in the preferred embodiment, other types of equipment could be used in place of the hydraulic turn cylinder 307 such as a setscrew, a rope-and-pulley system or the like. The belly bade 304 is mounted to the plow frame 301 by means of a hinge 308.

The belly blade 304 is rotatable 310 about the hinge 308 upon movement of the hydraulic ram 307. When the hydraulic ran 307 is extended, the belly blade 304 is rotated in a counterclockwise manner 310. Likewise, when the hydraulic ram 307 is contracted, the belly blade 304 is rotated in a counterclockwise manner 310 above the hinge 308.

FIGS. 9 and 10 depict the mounting frame 320 to mount the plow apparatus 300 to the belly blade apparatus 300 to the frame 160, 170 of the zero-turn machine 100. The top 312 of the mounting frame 320 is connected to the frame 160 or under carriage of the zero-turn machine 100 by a pair of bracket 319. The frame 320 includes a scissor lift mechanism 316 which includes a hydraulic lift (not shown) attached to the center 316(*a*) of the lift mechanism 316. The lift mechanism 316 also includes a belly blade apparatus mount 316(*b*) to mount the scissor lift mechanism 316 to the frame 301 of the belly blade apparatus 300. The scissor lift mechanism 316 operates to raise or lower the height of the belly blade 304 with respect to the ground. The mounting frame also includes a mounting frame support brace 315.

It is contemplated that the belly blade could be further adapted to accommodate an aerator roller attachment, a stripper roller attachment or a left rake attachment.

In embodiments of the inventions, the plow shovel may be interchangeable with a mower attachment. Such embodiments have the advantage of using the same zero-turn vehicle for plowing snow and also mowing grass. For example, the plow shovel may be attached to the vehicle during winter months, and the mower attachment may be attached during the remaining months of the year. The mower attachment may have a blade and a blade cover, wherein the gas engine propels the blade. The blade may be mounted inside the blade cover, and the blade cover, in turn, may be mounted to the vehicle's frame. In some embodiments, one set of bolts may fit both the plow shovel and the mower blade, allowing for easy interchangeability.

What is claimed is:

1. A zero radius turn vehicle, the vehicle comprising:
a frame having a front edge and a rear edge;
a pair of front wheels, the pair of front wheels comprising a left front wheel mounted on a left wheel mount extending from the front edge of the frame wherein the left front wheel is configured to rotate freely within the left wheel mount; and a right front wheel mounted on a right wheel mount extending from the front edge of the frame wherein the right front wheel is configured to rotate freely within the right wheel mount;
a pair of rear wheels mounted to a rear portion of the frame and controlled by steering rods configured to execute a zero-radius turn, the pair of rear wheels comprising a left rear wheel and a right rear wheel wherein a speed and direction of rotation control of the left rear wheel and a speed and direction of rotation control of the right rear wheel are controlled by the steering rods, wherein the steering rods operate independent of each other such that the left rear wheel operates independent of the right rear wheel wherein the left rear wheel and the right rear wheel move in opposite directions when executing the zero radius turn about the pair of front wheels and the pair of rear wheels;
the pair of front wheels are configured to permit the vehicle to execute the zero radius turn about the pair of front wheels and the pair of rear wheels;
an engine mounted to the frame and coupled to the pair of rear wheels;
a seat mounted to the frame and positioned between the pair of front wheels and the pair of rear wheels;
a plow frame mounted to the frame;
a plow shovel, the plow shovel being mounted to the plow frame between the pair of front wheels and the pair of rear wheels; and
a hinge connecting the plow frame to the plow shovel; and
a plow shovel control lever affixed to the plow shovel wherein the plow shovel control lever is configured to maneuver the position of the plow shovel around the hinge in relation to the frame.

2. The zero radius turn vehicle of claim 1, wherein the plow shovel control lever comprises a first hydraulic turn cylinder to position the plow shovel.

3. The zero radius turn vehicle of claim 2, wherein the plow shovel control lever includes a second hydraulic turn cylinder to position the plow shovel.

4. The zero radius turn vehicle of claim 3, wherein the first hydraulic turn cylinder and second hydraulic turn cylinder are controlled by a user-operated lever.

5. The zero radius turn vehicle of claim 1, wherein the pair of rear wheels are fitted with a soft tread aggressive drive tire.

6. The zero radius turn vehicle of claim 1, wherein the pair of rear wheels are configured to have a larger diameter than the pair of front wheels.

7. The zero radius turn vehicle of claim 4, wherein the vehicle is a riding lawn mower.

8. The zero radius turn vehicle of claim 1, wherein the engine is a gas engine connected to an air intake and an exhaust, and wherein the air intake and the exhaust are mounted behind the seat mounted to the frame.

9. The zero radius turn vehicle of claim 1, wherein the plow shovel is removably mounted to the frame.

10. The zero radius turn vehicle of claim 9, further comprising a mower attachment configured to be interchangeable with the plow shovel.

11. The zero radius turn vehicle of claim 1, wherein the plow shovel is adapted to accommodate an aerator roller.

12. The zero radius turn vehicle of claim 1, further comprising a stripper roller attachment configured to be interchangeable with the plow shovel, wherein the plow shovel is adapted to accommodate the stripper roller.

13. The zero radius turn vehicle of claim 1, further comprising a left rake attachment configured to be interchangeable with the plow shovel, wherein the plow shovel is adapted to accommodate the left rake attachment.

14. The zero radius turn vehicle of claim 1, further comprising a snow deflector attachment, wherein the plow shovel is adapted to accommodate the snow deflector.

15. The zero radius turn vehicle of claim 1, wherein the plow shovel control lever comprises a set screw.

16. The zero radius turn vehicle of claim 1, wherein the plow shovel control lever comprises a rope and pulley.

17. The zero radius turn vehicle of claim 1, wherein the plow shovel control lever comprises a hydraulic turn cylinder.

18. A zero radius turn vehicle for removing snow, the vehicle comprising:

a vehicle frame of a lawn mower, having a front edge portion and having a removable mower deck;

a pair of front wheels mounted to the vehicle frame and a pair of rear wheels mounted to the vehicle frame;

the pair of front wheels comprising a left front wheel mounted on a left mounting mechanism at the front edge portion of the frame wherein the left front wheel is configured to rotate freely within the left mounting mechanism; and a right front wheel mounted on a right mounting mechanism at the front edge portion of the frame wherein the right front wheel is configured to rotate freely within the right mounting mechanism;

the pair of rear wheels comprising a left rear wheel where a speed and direction of rotation are controlled by a left steering rod and a right rear wheel where a speed and direction are controlled by a right steering rod wherein the left steering rod operates independent of the right steering rod such that the when both the right steering rod and left steering rod are pushed forward simultaneously with a force, the left rear wheel and the right rear wheel move forward; when both the right steering rod and the left steering rod are pulled back simultaneously with the same force, the left rear wheel and the right rear wheel move backward and pushing either the right steering rod or the left steering rod forward while pulling the other steering rod back causes the wheels to move in opposite directions executing a zero radius turn about the pair of front wheels and the pair of rear wheels;

the pair of front wheels are configured to permit the vehicle to execute the zero radius turn about the pair of front wheels and the pair of rear wheels;

an engine mounted to the vehicle frame and coupled to one of the pair of front wheels or the pair of rear wheels to capable of powering the vehicle;

a stand-on frame connected to the vehicle frame in proximity to the pair of rear wheels;

a belly blade apparatus moveably fastened to the vehicle frame in a generally central location in the general location of the mower deck below the frame between the pair of front wheels and the pair of rear wheels;

the belly blade apparatus including a body having a frame mount wherein the belly blade apparatus is mounted to the vehicle frame at the frame mount;

the belly blade apparatus including a snowplow blade rotatably affixed to the frame mount of the belly blade body by a hinge mechanism;

a hydraulic cylinder affixed to the belly blade body and the snowplow blade, wherein the hydraulic cylinder is configured to rotate the blade about the rotatable hinge about a first axis relative to the frame; and a mechanism to move the snowplow blade about a second axis relative to the frame.

19. The vehicle for removing snow of claim 18, wherein the snowplow blade is configured to pivot about position the blade is moveably fastened to the vehicle frame in the generally central location.

20. The vehicle for removing snow of claim 18, the snowplow blade is positioned mid-way between the front wheels and the rear wheels at the center of gravity of the vehicle.

21. The vehicle for removing snow of claim 18, wherein the vehicle frame is configured to include a frontend weight box along the forward-most position of the frame.

22. The vehicle for removing snow of claim 18, wherein the pair of rear wheels is larger relative to the pair of front wheels.

23. The vehicle for removing snow of claim 19, further comprising a salt spreader positioned at the rearward-most position of the frame.

24. The vehicle for removing snow of claim 23, further comprising a frontend weight box affixed to the vehicle frame.

25. The vehicle for removing snow of claim 24, wherein the belly blade apparatus is removeable from the vehicle frame.

26. The vehicle for removing snow of claim 25, the vehicle frame is configured to accept a lawn mower platform.

27. The vehicle for removing snow of claim 26, wherein the lawn mower platform is attached to the vehicle frame.

* * * * *